(12) United States Patent
Graham et al.

(10) Patent No.: US 7,612,226 B2
(45) Date of Patent: Nov. 3, 2009

(54) AMINO ACID DERIVATIVES

(75) Inventors: Shelley Rene Graham, Ann Arbor, MI (US); Simon John Mantell, Sandwich (GB); David James Rawson, Sandwich (GB); Jacob Bradely Schwarz, Ann Arbor, MI (US)

(73) Assignee: Pfizer Inc., New York, NY (US)

( * ) Notice: Subject to any disclaimer, the term of this patent is extended or adjusted under 35 U.S.C. 154(b) by 126 days.

(21) Appl. No.: 11/414,422

(22) Filed: Apr. 28, 2006

(65) Prior Publication Data

US 2006/0247291 A1 Nov. 2, 2006

Related U.S. Application Data

(60) Provisional application No. 60/676,025, filed on Apr. 28, 2005.

(51) Int. Cl.
*C07C 261/00* (2006.01)
(52) U.S. Cl. .................... 560/159; 560/24; 548/495
(58) Field of Classification Search .................. None
See application file for complete search history.

(56) References Cited

U.S. PATENT DOCUMENTS

| | | | |
|---|---|---|---|
| 5,993,775 A | 11/1999 | Dean | |
| 6,162,824 A | 12/2000 | Ognyanov et al. | |
| 6,784,202 B1 * | 8/2004 | Pajouhesh et al. | 514/437 |
| 2002/0058646 A1 | 5/2002 | Lin et al. | |
| 2004/0147482 A1 * | 7/2004 | Pajouhesh et al. | 514/64 |
| 2005/0065176 A1 * | 3/2005 | Field et al. | 514/291 |
| 2006/0025471 A1 * | 2/2006 | Curry | 514/437 |
| 2006/0211741 A1 * | 9/2006 | Hanazawa et al. | 514/352 |
| 2006/0247291 A1 * | 11/2006 | Graham et al. | 514/400 |
| 2007/0129388 A1 * | 6/2007 | Rawson et al. | 514/267 |

FOREIGN PATENT DOCUMENTS

| | | |
|---|---|---|
| CS | 127852 * | 6/1968 |
| DE | 195 33 617 A1 | 9/1995 |
| EP | 03 336 305 A1 | 4/1988 |
| EP | 0 214 058 B1 | 5/1992 |
| EP | 0512848 A2 | 11/1992 |
| EP | 0 780 386 B1 | 6/1997 |
| EP | 0 926 135 B1 | 6/1999 |
| EP | 1584690 A1 | 10/2005 |
| GB | 2 263 109 A | 7/1993 |
| GB | 0504209 | 3/2005 |
| JP | 04-002899 | 1/1992 |
| JP | 05-001002 | 1/1993 |
| JP | 10-333511 | 12/1998 |
| JP | 2001-081013 | 3/2001 |
| JP | 2002-003431 | 1/2002 |
| JP | 2002-012571 | 1/2002 |
| JP | 2003-043678 | 2/2003 |
| JP | 2003-221328 | 8/2003 |
| WO | WO91/01724 | 2/1991 |
| WO | WO 91/17146 A1 | 11/1991 |
| WO | WO 94/08577 A1 | 4/1994 |
| WO | WO 94/12163 A1 | 6/1994 |
| WO | WO 95/15940 A1 | 6/1995 |
| WO | WO 95/15941 A1 | 6/1995 |
| WO | WO95/22557 | 8/1995 |
| WO | WO 98/14208 A1 | 4/1998 |
| WO | WO 98/17273 A1 | 4/1998 |
| WO | WO 99/45900 A1 | 9/1999 |
| WO | WO 00/37422 A2 | 6/2000 |
| WO | WO 00/37474 A1 | 6/2000 |
| WO | WO 00/40545 A1 | 7/2000 |
| WO | WO 00/43352 A1 | 7/2000 |
| WO | WO 00/44770 A1 | 8/2000 |
| WO | WO 00/59864 A1 | 10/2000 |
| WO | WO 01/09127 A1 | 2/2001 |
| WO | WO 01/17499 A1 | 3/2001 |
| WO | WO 01/17944 A1 | 3/2001 |
| WO | WO 01/48175 A2 | 7/2001 |
| WO | WO 01/87819 A1 | 11/2001 |
| WO | WO02/30871 | 4/2002 |
| WO | WO 02/078448 A1 | 10/2002 |
| WO | WO 03/011799 A1 | 2/2003 |
| WO | WO 03/097622 A2 | 11/2003 |
| WO | WO 2004/013112 A1 | 2/2004 |
| WO | WO2005/016331 A1 | 2/2005 |
| WO | WO2005/044780 A1 | 5/2005 |
| WO | WO2005/085179 A1 | 9/2005 |

(Continued)

OTHER PUBLICATIONS

Abshire et al. Preliminary Biological Studies of Several Aliphatic Amino Acid Analogs. J.MedChem (1972) 15(3) 226-29.*

(Continued)

*Primary Examiner*—Sikarl A. Witherspoon
*Assistant Examiner*—Chukwuma O Nwaonicha
(74) *Attorney, Agent, or Firm*—Gregg C. Benson; A. Dean Olson

(57) ABSTRACT

The present invention relates to a method of treating pain using a compound of formula

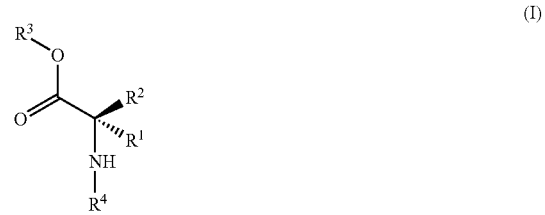

(I)

wherein $R^1$, $R^2$, $R^3$ and $R^4$ are as defined herein. The invention also relates to certain novel derivatives of formula (I).

9 Claims, No Drawings

FOREIGN PATENT DOCUMENTS

WO    WO 2006092691    9/2006

OTHER PUBLICATIONS

Agostini et al. Synthesis . . . Boll. Chim. Farm. 122 (1983) 86-95.*
Roos et al. JourOrgChem (1993) 58 (12) 3259-68.*
Berg et al. J.Pharm.Sci. Jan. 1977 19pages.*
Gee, Nicolas S., et al., "The Novel Anticonvulsant Drug, Gabapentin (Neurontin), Binds to the Subunit of a Calcium Channel", J. Biol. Chem., 1996, pp. 5768-5776, vol. 271, No. 10.
Gong, H.C., et al., "Tissue-specific Expression and Gabapentin-Binding Properties of Calcium Channel a2d Subunit Subtypes", J Membrane Biol., 2001, pp. 35-43, vol. 184, No. 1.
Marais, Elsé, et al., "Calcium Channel 2 SubunitsStructure and Gabapentin Binding", Mol Pharmacol, 2001, pp. 1243-1248, vol. 59, No. 5.
Qin, Ning, et al., "Molecular Cloning and Characterization of the Human Voltage-Gated Calcium Channel 2-4 Subunit", Mol Pharmacol, 2002, pp. 485-496, vol. 62, No. 3.
G. Sivagnanam, et al.; Arch. Int. Pharmacodyn, V.277, p. 168-176, 1985.
U.S. Appl. No. 60/675,761, filed Apr. 27, 2005, now lapsed.

* cited by examiner

AMINO ACID DERIVATIVES

This application is a U.S. non-provisional application, which claims the benefits of priority to U.S. Provisional Application No. 60/676,025, file Apr. 28, 2005.

This invention relates to α-amino acid derivatives derivatives. More particularly, this invention relates to α,α-disubstituted-α-amino acid derivatives and to processes for the preparation of, intermediates used in the preparation of, compositions containing and the uses of such derivatives.

The compounds of the present invention are alpha-2-delta (α2δ) receptor ligands (also known as alpha-2-delta ligands) and as such are useful in the treatment of a number of different diseases. An alpha-2-delta receptor ligand is a molecule which binds to any sub-type of the human calcium channel alpha-2-delta subunit. The calcium channel alpha-2-delta subunit comprises a number of sub-types which have been described in the literature (e.g. type 1, *J. Biol. Chem.*, 1996, 271(10), 5768-76; types 2 and 3, *J. Membr. Biol.*, 2001, 184 (1), 35-43 and *Mol. Pharmacol.*, 2001, 59(5), 1243-1248, 2001; and type 4, *Mol. Pharmacol.*, 2002, 62(3), 485-496). Alpha-2-delta receptor ligands are also sometimes known as GABA analogues.

Among known alpha-2-delta ligands are marketed drugs such as gabapentin (sold under the trade mark Neurontin) and pregabalin (sold under the trade mark Lyrica). Gabapentin is an anti-convulsant which is marketed for the treatment of epilepsy. Pregabalin is marketed for the treatment of neuropathic pain.

There is always a need to provide new drugs, which potentially have improved properties (e.g. greater potency, greater selectivity, better absorption from the gastrointestinal tract, greater metabolic stability and more favourable pharmacokinetic properties). Other potential advantages include greater or lesser penetration of the blood brain barrier, according to the disease targeted, lower toxicity and a decreased incidence of side-effects.

The invention therefore provides, as embodiment A, the use of a compound of formula (I):

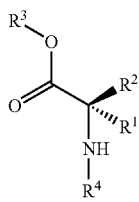

(I)

or a pharmaceutically acceptable salt or solvate thereof, wherein
$R^1$ is $C_1$-$C_6$ alkyl, said $C_1$-$C_6$ alkyl being optionally substituted by one or more halo, —$R^5$, —$OR^5$ or —$SR^5$ groups;
$R^2$ is methyl, optionally substituted by one or more fluoro groups;
$R^3$ is H, ($C_1$-$C_6$ alkyl), aryl, indanyl or ($C_1$-$C_6$ alkyl)oxycarbonyloxy($C_1$-$C_6$ alkyl);
$R^4$ is H, ($C_1$-$C_6$ alkyl)C(O)—, arylC(O)—, or a natural α-amino acid residue linked through its carboxyl group to form an amide;
$R^5$ is $C_1$-$C_6$ alkyl, $C_1$-$C_6$ haloalkyl, $C_3$-$C_8$ cycloalkyl or aryl; aryl is phenyl or naphthyl, each optionally substituted by one or more substituents selected from halo, —$NR^6R^6$, $C_1$-$C_6$ alkyl, $C_3$-$C_8$ cycloalkyl, $C_1$-$C_6$ alkoxy and cyano; and
$R^6$ is H, $C_1$-$C_6$ alkyl or $C_3$-$C_8$ cycloalkyl;

for the manufacture of a medicament for the treatment of pain.

The invention further provides, as embodiment B, a compound of formula (II):

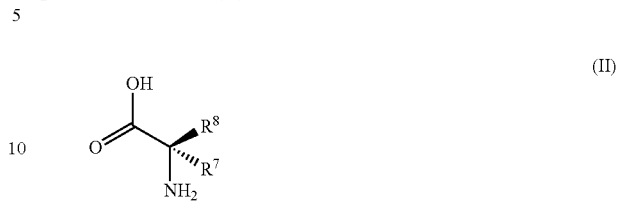

(II)

or a pharmaceutically acceptable salt or solvate thereof, wherein
$R^7$ is:
(a) branched $C_6$-$C_{10}$ alkyl, other than 4-methylpent-1-yl and 1-methylpent-1-yl;
(b) $C_2$-$C_6$ alkyl substituted by one or more flouro groups, other than 1-fluoroeth-1-yl, heptafluoropropyl, 2,2-ditrifluoromethyleth-1-yl, pentafluoroethyl, 2-fluoroeth-1-yl, 2-fluoropent-1-yl and 2-fluoro-3-methylbut-1-yl;
(c) $C_1$-$C_6$ alkyl substituted by one $C_3$-$C_8$ cycloalkyl group, other than cyclohexylmethyl;
(d) ethyl substituted by one aryl group, other than where aryl is phenyl or phenyl substituted by an —$NH_2$, iodo or methoxy group (regardless of other substitution);
(e) $C_3$-$C_4$ alkyl substituted by aryl, other than where aryl is phenyl, 3,4-dihydroxyphenyl or 3,4-dimethoxyphenyl;
(f) $C_5$-$C_6$ alkyl substituted by aryl;
(g) $C_1$-$C_2$ alkyl substituted by $C_5$-$C_6$ alkoxy;
(h) $C_3$-$C_6$ alkyl substituted by $C_1$-$C_6$ alkoxy;
(i) $C_1$-$C_6$ alkyl substituted by $C_3$-$C_8$ cycloalkyloxy;
(j) $C_1$-$C_6$ alkyl substituted by aryloxy, other than (2-methoxyphenyl)oxymethyl, (4-methoxyphenyl)oxymethyl, (4-chlorophenyl)oxymethyl, (2,6-dimethylphenyl)oxymethyl, (2-methoxy-5-chlorophenyl)oxymethyl, (2-methoxy-5-fluorophenyl)oxymethyl and (2-methoxy-4-chlorophenyl)oxymethyl;
(k) methyl substituted by hexylthio or $C_4$-$C_6$ alkyl substituted by $C_1$-$C_6$ alkylthio;
(l) $C_1$-$C_6$ alkyl substituted by $C_3$-$C_8$ cycloalkylthio, other than cyclohexylthiomethyl; or
(m) $C_1$-$C_6$ alkyl substituted by arylthio, other than phenylthiomethyl, (4-chlorophenyl)thiomethyl, (4-fluorophenyl)thiomethyl, 2-(phenylthio)ethyl, (4-chlorophenyl)thioethyl, (4-methoxyphenyl)thiomethyl and (4-methoxyphenyl)thioethyl;
$R^8$ is methyl, optionally substituted with one or more fluoro groups;
aryl is phenyl or naphthyl, each optionally substituted by one or more substituents selected from halo, —$NR^9R^9$, $C_1$-$C_6$ alkyl, $C_3$-$C_8$ cycloalkyl, $C_1$-$C_6$ alkoxy and cyano; and
$R^9$ is H, $C_1$-$C_6$ alkyl or $C_3$-$C_8$ cycloalkyl.

In the above definitions, halo means fluoro, chloro or bromo and is preferably fluoro or chloro. Alkyl and alkoxy groups containing the requisite number of carbon atoms can, unless otherwise specified, be unbranched or branched chain. Examples of alkyl include methyl, ethyl, n-propyl, i-propyl, n-butyl, i-butyl, sec-butyl and t-butyl. Examples of alkoxy include methoxy, ethoxy, n-propoxy, i-propoxy, n-butoxy, i-butoxy, sec-butoxy and t-butoxy. Examples of cycloalkyl include cyclopropyl, cyclobutyl, cyclopentyl, cyclohexyl and cycloheptyl.

In embodiment Aa, the invention provides the use of a compound of formula (I), or a pharmaceutically acceptable salt or solvate thereof, wherein $R^3$ and $R^4$ are both H and $R^1$ and $R^2$ are as defined above in embodiment A, for the manufacture of a medicament for the treatment of pain.

In embodiment Ab, the invention provides the use of a compound of formula (I), or a pharmaceutically acceptable salt or solvate thereof, wherein $R^3$ and $R^4$ are as defined above in embodiment A or embodiment Aa, $R^1$ is as defined in embodiment A and $R^2$ is methyl, for the manufacture of a medicament for the treatment of pain.

In embodiment Ac, the invention provides the use of a compound of formula (I), or a pharmaceutically acceptable salt or solvate thereof, wherein $R^3$ and $R^4$ are as defined above in embodiment A or embodiment Aa, $R^2$ is as defined above in embodiment A or embodiment Ab and $R^1$ is:
  (a) $C_1$-$C_2$ alkyl, said $C_1$-$C_2$ alkyl being optionally substituted by one or more halo, —$R^5$, —$OR^5$ or —$SR^5$ groups, $R^5$ being as defined in embodiment A; or
  (b) unsubstituted $C_5$-$C_7$ alkyl or $C_1$-$C_2$ alkyl substituted with one group selected from $C_3$-$C_8$ cycloalkyl, aryl or aryloxy, aryl being as defined in embodiment A;
  (c) branched, unsubstituted $C_5$-$C_7$ alkyl or $C_1$-$C_2$ alkyl substituted with one group selected from $C_3$-$C_8$ cycloalkyl, aryl or aryloxy, aryl being as defined in embodiment A;
  (d) ethylbutyl, dimethylbutyl, ethylpentyl, methylpentyl, methylbutyl, cyclopentylmethyl, cyclobutylmethyl, cyclopropylethyl, phenyloxyethyl or chlorophenylmethyl; or
  (e) 2-ethyl-but-1-yl, 3,3-dimethylbut-1-yl, 3-ethylpent-1-yl, 3-methylpent-1-yl, 2-methylbut-1-yl, 3-methylbut-1-yl, 4-methylpent-1-yl, cyclopentylmethyl, cyclobutylmethyl, 2-cyclopropyleth-1-yl, 2-(phenyloxy)eth-1-yl or (3-chlorophenyl)methyl;

for the manufacture of a medicament for the treatment of pain.

In embodiment Ba, the invention provides a compound of formula (II), or a pharmaceutically acceptable salt or solvate thereof, wherein $R^7$ is as defined above in embodiment B and $R^8$ is methyl.

In embodiment Bb, the invention provides a compound of formula (II), or a pharmaceutically acceptable salt or solvate thereof, wherein $R^8$ is as defined above in embodiment B or embodiment Ba and $R^7$ is:
  (a) branched $C_6$-$C_7$ alkyl, other than 4-methylpent-1-yl and 1-methylpent-1-yl; $C_1$-$C_2$ alkyl substituted by one $C_3$-$C_8$ cycloalkyl group, other than cyclohexylmethyl; $C_1$-$C_2$ alkyl substituted by aryloxy, other than (2-methoxyphenyl)oxymethyl, (4-methoxyphenyl)oxymethyl, (4-chlorophenyl)oxymethyl, (2,6-dimethylphenyl)oxymethyl, (2-methoxy-5-chlorophenyl)oxymethyl, (2-methoxy-5-fluorophenyl)oxymethyl and (2-methoxy-4-chlorophenyl)oxymethyl; 2-methylbutyl; or chlorophenylmethyl; or
  (b) 2-ethyl-but-1-yl, 3,3-dimethylbut-1-yl, 3-ethylpent-1-yl, 3-methylpent-1-yl, 2-methylbut-1-yl, 4-methylpent-1-yl, cyclopentylmethyl, cyclobutylmethyl, 2-cyclopropyleth-1-yl, 2-(phenyloxy)eth-1-yl or (3-chlorophenyl)methyl.

Specific preferred compounds according to the invention are those listed in the Examples section below and the pharmaceutically acceptable salts and solvates thereof.

Further examples of compounds for use in the invention are:
3-chloro-alpha-methyl-L-phenylalanine;
4-phenoxy-L-isovaline;
2,5-dimethyl-L-norleucine; and
(2S)-2-amino-4-cyclopropyl-2-methylbutanoic acid;

and the pharmaceutically acceptable salts and solvates thereof.

It should be noted that compounds of formula (II) are all also compounds of formula (I), being those compounds of formula (I) which are novel per se. Consequently, all references to compounds of formula (I) below should be understood to refer to compounds of formula (II) as well.

Pharmaceutically acceptable salts of compounds of formula (I) include the acid addition and base salts thereof.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see *Handbook of Pharmaceutical Salts: Properties, Selection, and Use* by Stahl and Wermuth (Wiley-VCH, Weinheim, Germany, 2002).

Pharmaceutically acceptable salts of a compound of formula (I) may be prepared by one or more of three methods:
  (i) by reacting the compound of formula (I) with the desired acid or base;
  (ii) by removing an acid- or base-labile protecting group from a suitable precursor of the compound of formula (I) or by ring-opening a suitable cyclic precursor, for example, a lactone or lactam, using the desired acid or base; or
  (iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

A compound of formula (I) in which $R^3$ and $R^4$ are H has a basic amino group and an acidic carboxy group and will exist, at physiological pH, as a zwitterion.

A compound of formula (I) may exist in both unsolvated and solvated forms. The term 'solvate' is used herein to describe a molecular complex comprising the compound of formula (I) and a stoichiometric amount of one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised.

For a review of such complexes, see J. Pharm. Sci., 64 (8), 1269-1288, by Haleblian (August 1975).

Hereinafter, all references to a compound of formula (I) include references to salts, solvates and complexes thereof and to solvates and complexes of salts thereof.

A compound of formula (I), as hereinbefore defined, may exist in one or more crystalline (polymorphic) or isomeric forms (including optical, geometric and tautomeric isomers), in an isotopically labelled form or as a prodrug. All such crystalline/isomeric forms and prodrugs are within the scope of the present invention and are further described below. All references to a compound of formula (I) should be interpreted accordingly.

Included within the scope of the invention are compounds of the formula (I) wherein $R^3$ and/or $R^4$ is a group which is converted to H following administration of the compound to a mammal (preferably a human). Such compounds are known as prodrugs. Thus, these derivatives, which may have little or no pharmacological activity themselves can, when administered into or onto the body, be converted into compounds of formula (I) wherein $R^3$ and $R^4$ are both H, such compounds having the desired activity as alpha-2-delta ligands. Such prodrugs can be converted, for example, by hydrolytic cleavage.

Typically, $R^3$ is an alkyl group, preferably a $C_1$-$C_6$ alkyl group. Specific examples of suitable alkyl groups are ethyl, isopropyl and n-butyl. Alternatively, $R^3$ can be an aryl group (wherein aryl is as defined above), such as phenyl, or an indanyl group. In other suitable embodiments $R^3$ can be an alkyloxycarbonyloxyalkyl group, such as —$CH_2OC(O)$ $O^tBu$, —$CH(CH_3)OC(O)OEt$ or —$CH(CH_3)OC(O)O^iPr$ (see *Journal of Pharmacology and Experimental Therapeutics*, 311, 1, 324-335) or a cyclic carbonate linked via a methylene group.

Typically, $R^4$ is an amide-forming group such as —$CO(C_1$-$C_6$ alkyl) or —$CO(aryl)$ (wherein aryl is as defined above). Specific examples are methylcarbonyl, isopropylcarbonyl and phenylcarbonyl. Alternatively, $R^4$ may be an α-amino acid residue joined through its carboxyl group to form an amide. The naturally occurring amino acids, particularly glycine, alanine and valine are preferred.

Whether or not a particular compound will act as a prodrug and be hydrolytically cleaved to the active compound in vivo may be accurately assessed using a number of in vitro tests and in vivo animal models. Prodrug hydrolysis can be characterised in vitro using a range of tissue fractions including simple homogenates and microsomes: see, for example, *Journal of Pharmacology and Experimental Therapeutics*, 294, 2, 580-587; *Life Sci.*, 62, 14, 1231-124; *International Journal of Pharmaceutics*, 166, 1, 45-53; and *Toxicol. Lett.*, 82-83, 439-445. Rat liver microsome homogenates are particularly useful in this regard. In vivo assays can also be used to investigate prodrug properties. Intravenous and oral pharmacokinetics with both the active principle and the prodrug provides information about the relative bioavailability of the prodrug, the ability of the body to hydrolyse the prodrug and the rate of hydrolysis to the active species (see *Antimicrob. Agents. Chemother.* 42, 3, 647-653). A proposed screening strategy for assaying prodrugs has been given in a recent review (Current Drug Metabolism, 2003, vol 4, no. 6, p 483).

Further information on the use of prodrugs may be found in *Pro-drugs as Novel Delivery Systems*, Vol. 14, ACS Symposium Series (T. Higuchi and W. Stella) and *Bioreversible Carriers in Drug Design*, Pergamon Press, 1987 (ed. E. B. Roche, American Pharmaceutical Association).

Prodrugs of compounds of the formula (I) other than those involving $R^3$ and $R^4$ groups are also within the scope of the invention and can, for example, be produced by replacing appropriate functionalities present in the compounds of formula (I) with certain moieties known to those skilled in the art as 'pro-moieties' as described, for example, in *Design of Prodrugs* by H. Bundgaard (Elsevier, 1985).

Some examples of other prodrugs in accordance with the invention include, where the compound of formula (I) contains a primary or secondary amino functionality (—$NH_2$ or —NHR where R≠H), an amide thereof, for example, a compound wherein, as the case may be, one or both hydrogens of the amino functionality of the compound of formula (I) is/are replaced by ($C_1$-$C_{10}$)alkanoyl.

Moreover, certain compounds of formula (I) may themselves act as prodrugs of other compounds of formula (I).

Also included within the scope of the invention are metabolites of compounds of formula (I), that is, compounds formed in vivo upon administration of the drug. Some examples of metabolites in accordance with the invention include (i) where the compound of formula (I) contains a methyl group, an hydroxymethyl derivative thereof (—$CH_3$→—$CH_2OH$):
(ii) where the compound of formula (I) contains an alkoxy group, an hydroxy derivative thereof (—OR→—OH);
(iii) where the compound of formula (I) contains a tertiary amino group, a secondary amino derivative thereof (—$NR^1R^2$→—$NHR^1$ or —$NHR^2$);
(iv) where the compound of formula (I) contains a secondary amino group, a primary derivative thereof (—$NHR^1$→—$NH_2$);
(v) where the compound of formula (I) contains a phenyl moiety, a phenol derivative thereof (-Ph→-PhOH); and Compounds of formula (I) containing a further asymmetric carbon atom can exist as diastereomers. Where structural isomers are interconvertible via a low energy barrier, tautomeric isomerism ('tautomerism') can occur. This can take the form of proton tautomerism or so-called valence tautomerism. It follows that a single compound may exhibit more than one type of isomerism.

Included within the scope of the present invention are all diastereomers, and tautomeric forms of the compounds of formula (I), including compounds exhibiting more than one type of isomerism, and mixtures of one or more thereof. Also included are acid addition or base salts wherein the counterion is optically active, for example, d-lactate or l-lysine, or racemic, for example, dl/tartrate or dl-arginine.

Diastereomers may be separated by conventional techniques well known to those skilled in the art, for example, chromatography and fractional crystallisation.

Compounds of the formula (I) are α-amino acids with a defined stereochemistry at the α-carbon atom. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound. The resulting diastereomeric mixture may be separated by chromatography and/or fractional crystallization and one or both of the diastereoisomers converted to the corresponding pure enantiomer(s) by means well known to a skilled person.

Enantiomerically-enriched compounds may also be obtained using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

Stereoisomeric conglomerates may be separated by conventional techniques known to those skilled in the art—see, for example, *Stereochemistry of Organic Compounds* by E. L. Eliel and S. H. Wilen (Wiley, New York, 1994).

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

The compounds of formula (I), being alpha-2-delta receptor ligands, are potentially useful in the treatment of a wide range of disorders. The treatment of pain, particularly neuropathic pain, is a preferred use.

Physiological pain is an important protective mechanism designed to warn of danger from potentially injurious stimuli from the external environment. The system operates through a specific set of primary sensory neurones and is activated by noxious stimuli via peripheral transducing mechanisms (see Millan, 1999, Prog. Neurobiol., 57, 1-164 for a review). These sensory fibres are known as nociceptors and are characteristically small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually in twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a hightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:
pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;
heart and vascular pain, including pain caused by angina, myocardical infarction, mitral stenosis, pericarditis, Raynaud's phenomenon, scleredoma and skeletal muscle ischemia;
head pain, such as migraine (including migraine with aura and migraine without aura), cluster headache, tension-type headache mixed headache and headache associated with vascular disorders; and
orofacial pain, including dental pain, otic pain, burning mouth syndrome and temporomandibular myofascial pain.

The compounds of formula (I) are potentially useful in the treatment of all kinds of pain but are particularly useful in the treatment of neuropathic pain.

Apart from pain, the compounds of formula (I) are potentially useful in the treatment of any disease or condition which is treatable using an alpha-2-delta ligand. Such conditions include epilepsy, gastrointestinal disorders, premature ejaculation, burning mouth syndrome, bladder disorders (such as over active bladder), faintness attacks, fibromyalgia, hypokinesia, cranial disorders, hot flashes, essential tremor, chemical dependencies and addictions, withdrawal symptoms associated with dependencies or addictions, addictive behaviours, spasticity, arthritis, inflammatory disorders (e.g. rheumatoid arthritis, osteoarthritis, psoriasis), diuresis, premenstrual syndrome, premenstrual dysphoric disorder, tinnitus, gastric damage, Down's syndrome, demyelinating diseases (e.g. multiple sclerosis and amylolateral sclerosis), cerebral vascular disorders due to acute or chronic cerebrovascular damage (e.g. cerebral infarction, subarachnoid haemorrhage or cerebral oedema), head trauma, spinal cord trauma and neuronal damage that occurs, for instance, during stroke, in cardiac bypass surgery, in incidents of intracranial hemorrhage, in perinatal asphyxia, in cardiac arrest and in status epilepticus. Alpha-2-delta ligands may also be useful in the treatment of delirium, dementia and amnestic and other cognitive or neurodegenerative disorders (e.g. Parkinson's disease, Huntington's disease, Alzheimer's disease, senile dementia, memory disorder, vascular dementia). They may be useful in the treatment of movement disorders such as akinesias, dyskinesias, spasticities, Tourette's syndrome, Scott syndrome, palsys, akinetic-rigid syndrome and extra-pyramidal movement disorders. They may also be useful in the treatment of sleep disorders, mood disorders, depression, depressive disorders, bipolar disorders, anxiety disorders, panic, borderline personality disorder, schizophrenia, psychotic disorders, behavioural disturbances associated with mental retardation, autistic disorder and conduct disorders.

All of the compounds of formula (I) can be prepared by conventional routes such as by the procedures described in the general methods presented below or by the specific methods described in the Examples section and the Preparations section, or by similar methods thereto. The present invention also encompasses any one or more of these processes for preparing the compounds of formula (I), in addition to any novel intermediates used therein.

In the following general methods, $R^1$, $R^2$, $R^3$ and $R^4$ are as previously defined for a compound of formula (I) unless otherwise stated and Ph is phenyl.

According to a first process, (A), a compound of formula (I), wherein $R^3$ and $R^4$ are H, may be prepared by the hydrogenolytic deprotection of a compound of formula (III)

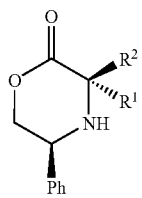

(III)

wherein $R^1$ and $R^2$ are as defined above. The hydrogenation is typically carried out using a source of hydrogen such as hydrogen gas, cyclohexadiene or ammonium formate (preferably hydrogen gas) and a transition metal catalyst such as a palladium, platinum or rhodium catalyst (preferably a palladium catalyst). An acid, such as hydrochloric or trifluoroacetic acid, may also be used to increase the rate of reaction. In a preferred procedure, a solution of the compound of formula (III) in a suitable solvent, such as ethanol, is treated with palladium on carbon and hydrochloric acid hydrogenated at about 414 kPa (60 psi).

A compound of formula (III) may be prepared by treating an imine of formula (IV):

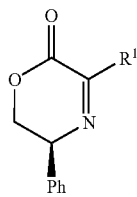

(IV)

wherein $R^1$ is as defined above, with a compound of formula:

(V)

wherein $R^2$ is as defined above and $M^1$ is a suitable metal, optionally bearing one or more further ligands; or by treating an imine of formula (VI):

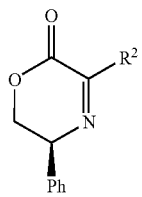

(VI)

wherein $R^2$ is as defined above, with a compound of formula:

(VII)

wherein $R^1$ and $M^1$ are as defined above. In such an imine addition reaction the organometallic reagent of formula (V) or (VII) is typically an organolithium or an organomagnesium derivative. An organomagnesium (Grignard) reagent, wherein $M^1$ is MgX, X being a halide, is preferred. The reaction is carried out in a suitable inert solvent such as tetrahydrofuran or diethyl ether at low temperature, typically between 0 and −78° C. In a preferred procedure, a solution of the compound of formula (IV) or (VI) in a suitable solvent, such as tetrahydrofuran, is treated with a suitable Grignard reagent of formula (V) or (VII), respectively, at −50° C. and in the presence of boron trifluoride etherate.

Compounds of formula (IV) and (VI) can be prepared by the condensation of a compound of formula:

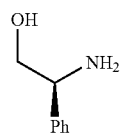

(VIII)

with, respectively, a compound of formula:

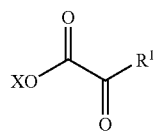

(IX)

wherein $R^1$ is as defined above and X is $C_1$-$C_6$ alkyl; or a compound of formula (X):

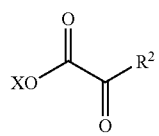

(X)

wherein $R^2$ is as defined above and X is $C_1$-$C_6$ alkyl. The condensation may be carried out under basic, neutral or acidic conditions and generally requires elevated temperatures and/or prolonged reaction times. In a typical procedure, a solution of the compound of formula (VII) and the compound of formula (IX) or (X), in a suitable solvent, such as trifluoroethanol, is heated at about 80° C. in the presence of a dehydrating agent such as 4A molecular sieves.

Compounds of formula (X), (IX) and (VIII) are either commercially available or easily prepared by standard methods well known to the skilled person, either as a result of common general knowledge (e.g. see 'Comprehensive Organic Transformations' by Richard Larock (1999, VCH Publishers Inc.) or by reference to specific published procedures.

Compounds of formula (I) wherein $R^3$ and/or $R^4$ are not H may be prepared from compounds of formula (I) wherein $R^3$ and/or $R^4$ are H by simple chemical transformations well known to the skilled man. Suitable conditions for such amide and ester forming reactions may be found in Comprehensive Organic Transformations referenced above.

Alternatively, according to a second process, (B), a compound of formula (I), wherein $R^3$ and $R^4$ are H, may be prepared by hydrogenolytic deprotection of a ring-opened compound of formula (IIIa)

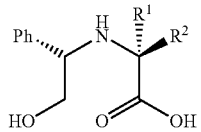

(IIIa)

wherein $R^1$ and $R^2$ are as defined above. The hydrogenation is typically carried out using a source of hydrogen such as hydrogen gas, cyclohexadiene or ammonium formate (preferably hydrogen gas) and a transition metal catalyst such as a palladium, platinum or rhodium catalyst (preferably a palladium catalyst). An acid, such as hydrochloric or trifluoroacetic acid, may also be used to increase the rate of reaction. In a preferred procedure, a solution of the compound of formula (IIIa) in a suitable solvent, such as propan-2-ol and water, is treated with palladium on carbon and hydrogenated at about 414 kPa (60 psi).

A compound of formula (IIIa) may be prepared by treating an imine of formula (IV) or (VI) with a compound of formula (V) or (VII) followed by treatment with a suitable acid or base. Suitable conditions for such an imine addition reaction are as described above for process (A). In a preferred procedure, a solution of the compound of formula (VI) in a suitable solvent, such as tetrahydrofuran, is first treated with a suitable Grignard reagent of formula (VII) at −78° C. in the presence of boron trifluoride tetrahydrofuran complex, followed by treatment with a suitable acid such as aqueous hydrochloric acid.

According to a third process, (C), a compound of formula (I), wherein $R^3$ and $R^4$ are both H, may alternatively be prepared by the hydrolysis of a nitrile of formula (XI):

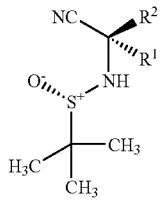

(XI)

wherein $R^1$ and $R^2$ are as defined above. The hydrolysis is typically accomplished with acidic or basic catalysis in an aqueous solvent at an elevated temperature. In a typical procedure, a solution of the compound of formula (XI) in water is treated with 6 molar hydrochloric acid and heated to about 100° C.

A compound of formula (XI) may be prepared by the addition of cyanide to a compound of formula (XII):

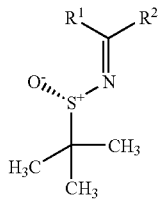

(XII)

wherein $R^1$ and $R^2$ are as defined above. A preferred source of cyanide for the addition is a compound of formula $M^2CN$ wherein $M^2$ is a metal cation, optionally bearing other ligands. Most preferred is a dialkylaluminium cyanide such as diethylaluminium cyanide. The reaction is carried out as a solution in a suitable inert solvent such as tetrahydrofuran, dichloromethane or diethyl ether. In a preferred procedure a solution of a compound of formula (XII) in a mixture of isopropanol and tetrahydrofuran is treated with diethylaluminium cyanide at a temperature of between −78 and −20° C.

A compound of formula (XII) may be prepared by the reaction of a compound of formula (XIII)

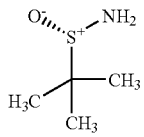

(XIII)

with a compound of formula (XIV):

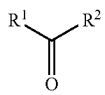

(XIV)

wherein $R^1$ and $R^2$ are as defined above, under dehydrating conditions. Typically the reaction is catalysed by a Lewis acid (e.g. titanium tetraethoxide). In a preferred procedure, a solution of the compound of formula (XIII) and the compound of formula (XIV) in a suitable solvent (such as tetrahydrofuran) is treated with titanium tetraethoxide at a temperature of about 50° C.

Compounds of formula (XIII) and (XIV) are either commercially available or easily prepared by standard methods well known to the skilled person, either as a result of common general knowledge (e.g. see 'Comprehensive Organic Transformations' by Richard Larock (1999, VCH Publishers Inc.) or by reference to specific published procedures.

According to a fourth process, (D), a compound of formula (I), wherein $R^3$ and $R^4$ are both H, may alternatively be prepared by the hydrolysis of an ester of formula (XV):

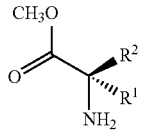

(XV)

wherein $R^1$ and $R^2$ are as defined above. The hydrolysis may be carried out under acidic or basic conditions. In a typical procedure, a solution of a compound of formula (XV) in aqueous hydrochloric acid is heated under reflux for 16 hours.

A compound of formula (XV) may be prepared by the methanolysis of a compound of formula (XVI):

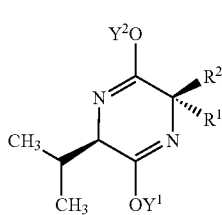

(XVI)

wherein $R^1$ and $R^2$ are as defined above and $Y^1$ and $Y^2$ are each selected from $C_1$-$C_6$ alkyl. The reaction may be carried out with acid or base catalysis. In a typical procedure, a solution of a compound of formula (XVI) in methanolic hydrochloric acid is stirred at room temperature for about 72 hours.

A compound of formula (XVI) may be prepared by the alkylation of a compound of formula (XVII):

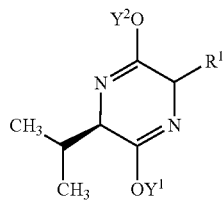

(XVII)

wherein $R^1$, $Y^1$ and $Y^2$ are as defined above, with a compound of formula $R^2L^1$, wherein $R^2$ is as defined above and $L^1$ is a suitable leaving group. $L^1$ is preferably halo (particularly bromo), trifluoromethanesulphonate or methanesulphonate. Typically, the compound of formula (XVII) is deprotonated with a base, such as butyl lithium, in an inert solvent such as diethyl ether or tetrahydrofuran, at low temperature (usually in the range −78 to −20° C.). A solution of the alkylating agent in an inert solvent is then added. In a preferred procedure, a solution of the compound of formula (XVII) in tetrahydrofuran is treated with n-butyl lithium at −78° C. and an excess of the alkylating agent is then added.

A compound of formula (XVII) may be prepared by the double alkylation of a compound of formula (XVIII):

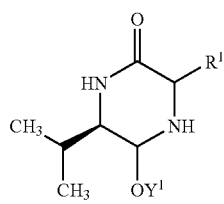

(XVIII)

wherein $R^1$ is as defined above. Typically, the compound of formula (XVIII) is deprotonated using a base (e.g. potassium tert-butoxide, potassium hexamethyldisilazide or sodium hydride) in an inert solvent, such as tetrahydrofuran or diethyl ether. A suitable alkylating agent, such as an alkyl halide (particularly an alkyl bromide) or an alkyl sulphonate ester (e.g. an alkyl mesylate) is then added at a temperature of from −20° C. to room temperature. In a preferred procedure, an excess of trimethoxonium tetrafluoroborate in is used as the alkylating agent.

A compound of formula (XVIII) may be prepared by the cyclisation of a compound of formula (XIX):

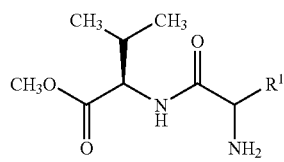

(XIX)

wherein $R^1$ is as defined above. In a typical procedure, a solution of a compound of formula (XIX) in a suitable solvent, such as toluene, is heated under reflux.

A compound of formula (XIX) may be prepared by the reduction of a compound of formula (XX):

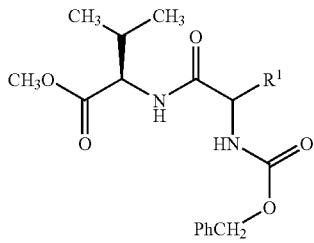

(XX)

wherein $R^1$ is as defined above. The reduction is typically accomplished using hydrogen and a hydrogenation catalyst such as a palladium, platinum or rhodium catalyst. In a preferred procedure, a solution of the compound of formula (XX) in a suitable solvent, such as aqueous ethanolic hydrochloric acid, is treated with hydrogen at room temperature.

A compound of formula (XX) may be prepared by coupling an amine of formula (XXI):

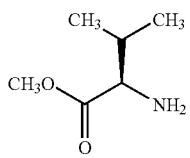

(XXI)

with an acid of formula (XXII):

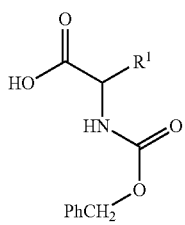

(XXII)

wherein $R^1$ is as defined above. The acid is first activated, either by conversion to the corresponding acid chloride or by treatment with a suitable peptide coupling agent. If the acid chloride is used it is preformed and then reacted with the amine as a solution in a suitable inert solvent (such as dichloromethane or tetrahydrofuran) in the presence of a base (such as triethylamine). Alternatively, as solution of the acid and the amine in a suitable solvent (such as dichloromethane or tetrahydrofuran) is treated with a base (such as triethylamine) and a coupling agent (such as a carbodiimide).

Compounds of formula (XXI) and (XXII) are either commercially available or easily prepared by standard methods well known to the skilled person, either as a result of common general knowledge (e.g. see 'Comprehensive Organic Transformations' by Richard Larock (1999, VCH Publishers Inc.) or by reference to specific published procedures.

According to a fifth process, (E), a compound of formula (I), wherein $R^3$ and $R^4$ are both H, $R^1$ and $R^5$ are not substituted by halo or cyano, and $R^2$ is methyl, may alternatively be prepared by resolution of a racemic compound of formula (Ia).

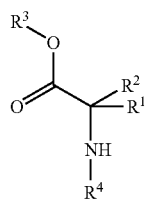

(Ia)

Resolution may be carried out by a number of methods known to a person skilled in the art, including chiral chromatography, formation of diasteroemeric derivatives (such as esters, ethers or salts), or chemical or enzymatic kinetic resolution. Typically, a compound of formula (Ia) is treated with a chiral base or acid in a suitable organic solvent to form diastereomeric salts and separation is achieved by crystallisation of the least soluble diastereoisomer. Suitable resolving agents include tartaric acid derivatives, mandelic acid, camphorsulfonic acid, sparteine, alpha-methylbenzylamine, pseudoephedrine and aminoalcohols. Diastereomeric salt resolution may also be used to increase the enantiomeric excess of a non-racemic compound of formula (I).

A compound of formula (Ia), wherein $R^a$ is aryl, optionally substituted with amino, ($C_1$-$C_6$)alkylamino, hydroxyl, ($C_1$-$C_6$)alkoxy, sulfonate, sulphonamide, sulfonyl, trifluoromethyl, nitro, ($C_1$-$C_6$)acyl or nitrile, and $R^b$ is hydrogen, ($C_1$-$C_6$)alkyl or $R^a$, may be prepared from a compound of formula (XXIII) by hydrogenolytic deprotection

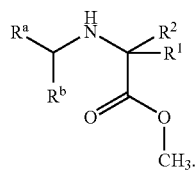

(XXIII)

Hydrogenolytic deprotection conditions are as described above for process (A).

Alternatively, a compound of formula (I) can be prepared from a compound of formula (XXIII) by resolution of the compound of formula (XXIII) followed by hydrogenolytic deprotection.

A compound of formula (XXIII) may be prepared by treating a compound of formula (XXIV)

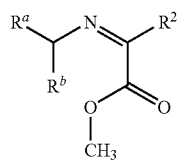

(XXIV)

with a compound of formula (VII) as defined above. Suitable conditions for the imine addition reaction are as defined above for process (A). An organomagnesium (Grignard) reagent, wherein $M^1$ is MgX, X being a halide, is preferred. In a preferred procedure, a solution of the compound of formula (XXIV) in a suitable solvent, such as tetrahydrofuran, is treated with a suitable Grignard reagent of formula (VII) at low temperature, typically at a temperature of from 0 to $-78°$ C. and in the presence of boron trifluoride etherate or boron trifluoride tetrahydrofuran complex.

A compound of formula (XXIV) may be prepared by condensation of an ester compound of formula (X), as defined in process (A), with an amine compound of formula (XXV) in the presence of a suitable catalyst.

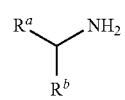

(XXV)

Conditions are as described for process (A). Compounds of formula (XXV) are commercially available.

According to a sixth process (F), a compound of formula (I), wherein $R^3$ and $R^4$ are both H, $R^1$ and $R^5$ are not substituted by halo or cyano, and $R^2$ is methyl, may be alternatively prepared by deprotection of a compound of formula (XXVI)

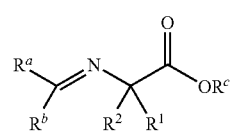

(XXVI)

wherein $R^a$ and $R^b$ are as defined for process (E) and $R^c$ is a suitable chiral ester group, such as mentyl or pseudoephidrinyl. The deprotection may be carried out under acidic or basic conditions, typically aqueous hydrochloric acid and diethyl ether or aqueous citric acid and tetrahydrofuran.

Compounds of formula (XXVI) may be prepared as described in Tetrahedron: Asymmetry, 1992, 3, 591-594 and Tetrahedron Letters, 1982, 23, 4259-4262.

Alternatively, a racemic compound of formula (Ia) may be prepared by an analogous process wherein $R^c$ is an achiral ester group such as $C_{1-6}$ alkyl or benzyl.

A compound of formula (XXVI) may be prepared by reaction of a compound of formula (XXVII) with an electrophile of formula (XXVIII) under basic conditions

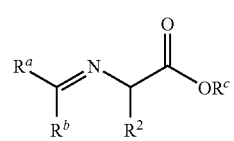

(XXVII)

(XXVIII)

LG—$R^1$ wherein LG is a suitable leaving group such as Cl, Br, I, or $R^dSO_2O$ wherein $R^d$ is $C_1$-$C_6$ alkyl, $CF_3$, or aryl optionally substituted with $C_1$-$C_6$ alkyl or nitro, preferably Br or trifluoromethanesulfonyl. Additionally, an additive such as potassium iodide may be used to form a more reactive electrophile in-situ. Typically the reaction is carried out using an inorganic base such as potassium carbonate or sodium hydroxide, or an organic base such as a phosphazene base, optionally in the presence of a phase transfer catalyst, in an organic solvent such as dichloromethane, tetrahydrofuran or toluene at a temperature of from −78° C. to room temperature.

Compounds of the formula (XXVII) may be prepared as described in Tetrahedron, 2004, 60, 5919-5930 and Tetrahedron Letters, 1998, 39, 8775-8778.

A compound of formula (XXVII) may also be prepared by isomerisation of a compound of formula (XXIV) which itself is prepared from an amine compound of formula (XXV) by a process analogous to that described in process (E).

Alternatively, a compound of formula (XXVI) may be prepared by methylation of a compound of formula (XXIX)

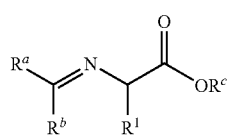

(XXIX)

Typical conditions comprise treating a compound of formula (XXIX) with a suitable electrophile (e.g. methyl iodide, dimethyl sulfate, trimethyloxonium tetrafluoroborate, or methyl triflate) and an inorganic base, such as potassium carbonate or sodium hydroxide, or an organic base, such as a phosphazene base, optionally in the presence of a phase transfer catalyst, in an organic solvent, such as dichloromethane, tetrahydrofuran or toluene, at a temperature of from −78° C. to room temperature.

A compound of formula (XXIX) may be prepared by reaction of a compound of formula (XXX) with an electrophile of formula (XXVIII) under basic conditions as described above for process (F).

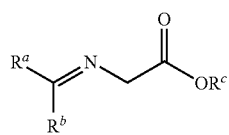

(XXX)

Alternatively, compounds of the formula (XXIX) may be prepared as described in Tetrahedron, 2004, 60, 5919-5930 and Tetrahedron Letters, 1998, 39, 8775-8778.

Compounds of the formula (XXX) may be prepared as described in J. Org. Chem, 1982, 47, 2663-2666.

According to a seventh process (G), a racemic compound of formula (Ia) wherein $R^3$ and $R^4$ are both H, $R^1$ and $R^5$ are not substituted by halo or cyano, and $R^2$ is methyl, may be alternatively prepared by condensation of a compound of formula (XXXI) with an ammonium source or amine and a cyanide source, followed by hydrolysis of the resulting aminonitrile or hydantoin.

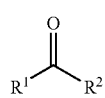

(XXXI)

The condensation may be carried out using an ammonia source such as ammonium acetate or ammonium carbonate, or an amine $R^e NH_2$, wherein $R^e$ is $C_1$-$C_6$ alkyl, benzyl, or aryl optionally substituted with amino, ($C_1$-$C_6$ alkyl)amino, hydroxyl, $C_1$-$C_6$ alkoxy, sulfonate, sulfonamido, sulfonyl, $CF_3$, nitro, $C_1$-$C_6$ acyl or nitrile, and an acyl anion equivalent such as a cyanide salt. Typical conditions for hydrolysis comprise treating the resulting aminonitrile or hydantoin with either acid or base in an aqueous solvent system. Typically the aminonitrile or hydantoin is treated with aqueous hydrochloric, hydrobromic, sulphuric or phosphoric acid, or aqueous potassium hydroxide or sodium hydroxide containing 6 to 12% hydrogen peroxide, at a temperature of from room temperature to 100° C.

Alternatively, the condensation step may be carried out either on the ketone or on a suitable ketone derivative such as a phosphinylimine in the presence of a chiral catalyst (such as a lanthanide-BINOL derived catalyst or a cyclohexyldiamine derived catalyst) or a chiral ketone derivative of the compound of formula (XXXI), such as a chiral imine, or sulfinylimine, may be used to provide a compound of formula (I) in a stereoselective manner.

According to an eighth process, (H), a compound of formula (I) wherein $R^3$ and $R^4$ are both H, $R^1$ and $R^5$ are not substituted by halo or cyano, and $R^2$ is methyl, may be alternatively prepared by Hoffmann rearrangement of a compound of formula (XXXII)

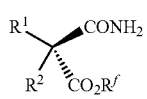

(XXXII)

wherein $R^f$ is H, $C_1$-$C_{10}$ alkyl, benzyl or substituted benzyl. The Hoffmann rearrangement is suitably carried out using sodium hypobromite or a mixture of aqueous sodium hydroxide and bromine. Alternatively, phenyliodosylbis(triflate) in a mixture of acetonitrile and water at room temperature will effect this transformation.

A compound of formula (XXXII) may be prepared by desymmetrisation of a compound of formula (XXXIII)

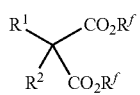

(XXXIII)

wherein $R^f$ is as defined above or a compound of formula (XXXV)

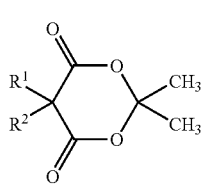

(XXXV)

by selective reaction of one of the ester groups with ammonia or an ammonia source such as ammonium chloride, or a suitably protected amine followed by deprotection. Alternatively, the desymmetrisation may be effected by hydrolysis of one of the ester groups to the carboxylic acid followed by amide coupling (for example using 1,1'-carbonyl diimidazole and ammonia in acetonitrile at room temperature) to give a compound of formula (XXXII) (see Angewandte Chemie, International Edition (2004), 43(47), 6493-6496). The desymmetrisation may be carried out either using an enzyme (for example a lipase such as pig liver esterase or *Candida Antarctica* in an aqueous or ammonia based solvent system) or chemically (for example using alpha-methyl benzylamine followed by hydrogenolysis using palladium on carbon and hydrogen in an alcoholic solvent at room temperature or above, or using a chiral catalyst and a suitable amine or ammonia source).

Compounds of formula (XXXIII) and (XXXV) can be prepared from commercially available compounds of formula (XXXIV) by reaction with suitable electrophiles of formula (XXVIII) under basic conditions as described in procedure F

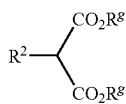

(XXXIV)

wherein $R^g$ is H, $C_1$-$C_{10}$ alkyl, benzyl or substituted benzyl, or the two $R^g$ groups taken together are $C(CH_3)_2$.

Alternatively, compounds of formula (XXXIII) and (XXXV) can be prepared from commercially available compounds of formula (XXXVI)

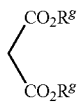

(XXXVI)

wherein $R^g$ is as defined above, by reaction with suitable electrophiles of formula (XXVIII) under basic conditions followed by methylation with a suitable reagent as described in procedure F.

Alternatively, a compound of formula (Ia) can be prepared by Hoffman rearrangement of a compound (XXXIIa)

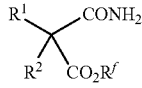

(XXXIIa)

wherein $R^f$ is as defined above. Conditions are as described for process (H) above.

Racemic compounds of formula (XXXIIa) can be prepared from compounds of formula (XXXIII) or (XXXV) using the conditions described for process (H) above, but in the absence of an enantioselective catalyst or chiral reagent.

Compounds of formula (I) can also be prepared by using the reactions described above to construct a compound wherein $R^1$ or $R^2$ are partially formed and then completing the synthesis by functional group manipulation. For instance, a group may be carried through the synthesis in a protected form and deprotected in a final step. Suitable protecting groups are described in 'Protective Groups in Organic Synthesis' by Theodora Greene and Peter Wuts (third edition, 1999, John Wiley and Sons). Suitable functional group transformations are described in 'Comprehensive Organic Transformations' by Richard Larock (1999, VCH Publishers Inc.).

Compounds of formula (I) may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of formula (I) or in combination with one or more other drugs (or as any combination thereof). Generally, they will be administered as a formulation in association with one or more pharmaceutically acceptable excipients. The term 'excipient' is used herein to describe any ingredient other than a compound of formula (I). The choice of excipient will to a large extent depend on factors such as the particular mode of administration, the effect of the excipient on solubility and stability, and the nature of the dosage form.

Pharmaceutical compositions suitable for the delivery of compounds of formula (I) and methods for their preparation will be readily apparent to those skilled in the art. Such compositions and methods for their preparation may be found, for example, in *Remington's Pharmaceutical Sciences,* 19th Edition (Mack Publishing Company, 1995).

A compound of formula (I) may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, powders, lozenges (including liquid-filled lozenges), chews, multi- and nano-particulates, gels, solid solutions, liposomes, films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose or a suitable oil, and one or more emulsifying agents and/or suspending agents. Liquid formulations may also be prepared by the reconstitution of a solid, for example, from a sachet.

A compound of formula (I) may also be used in fast-dissolving, fast-disintegrating dosage forms such as those described in Expert Opinion in Therapeutic Patents, 11 (6), 981-986, by Liang and Chen (2001).

For tablet dosage forms, depending on dose, a compound of formula (I) may make up from 1 weight % to 80 weight % of the dosage form, more typically from 5 weight % to 60 weight % of the dosage form. In addition to the compound of formula (I), tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (as, for example, the monohydrate, spray-dried monohydrate or anhydrous form), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% of a compound of formula (I), from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in *Pharmaceutical Dosage Forms: Tablets*, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula (I), a film-forming polymer, a binder, a solvent, a humectant, a plasticiser, a stabiliser or emulsifier, a viscosity-modifying agent and a solvent. Some components of the formulation may perform more than one function.

A compound of formula (I) for use in a film may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, a compound of formula (I) may be used in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients in such a film include anti-oxidants, colorants, flavourings, flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed, sustained, pulsed, controlled, targeted and programmed release formulations.

Suitable modified release formulations for the purposes of the invention are described in U.S. Pat. No. 6,106,864. Details of other suitable release technologies such as high energy dispersions and osmotic and coated particles are to be found in *Pharmaceutical Technology On-line*, 25(2), 1-14, by Verma et al (2001). The use of chewing gum to achieve controlled release is described in WO-A-00/35298.

A compound of formula (I) may also be administered directly into the blood stream, into muscle, or into an internal organ. Suitable routes for such parenteral administration include intravenous, intraarterial, intraperitoneal, intrathecal, intraventricular, intraurethral, intrasternal, intracranial, intramuscular and subcutaneous delivery. Suitable means for parenteral administration include needle (including microneedle) injectors, needle-free injectors and infusion techniques.

Parenteral formulations are typically aqueous solutions which may contain excipients such as salts, carbohydrates and buffering agents (preferably at a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of a compound of formula (I) used in the preparation of a parenteral formulation may be increased by the use of appropriate formulation techniques, such as the incorporation of solubility-enhancing agents.

Formulations for parenteral administration may be formulated to be immediate and/or modified release. Modified release formulations include delayed, sustained, pulsed, controlled, targeted and programmed release formulations. Thus, a compound of formula (I) may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

A compound of formula (I) may also be administered topically to the skin or mucosa, i.e. dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J. Pharm. Sci., 88 (10), 955-958, by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed, sustained, pulsed, controlled, targeted and programmed release formulations.

A compound of formula (I) can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of a compound of formula (I) comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, a drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of a compound of formula (I), a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of a compound of formula (I) per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations intended for inhaled/intranasal administration.

Formulations for inhaled/intranasal administration may be formulated to be immediate and/or modified release using, for example, PGLA. Modified release formulations include delayed, sustained, pulsed, controlled, targeted and programmed release formulations.

In the case of dry powder inhalers and aerosols, the dosage unit is determined by means of a valve which delivers a metered amount. Units in accordance with the invention are typically arranged to administer a metered dose or "puff". The overall daily dose will be administered in a single dose or, more usually, as divided doses throughout the day.

A compound of formula (I) may be administered rectally or vaginally, e.g. in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed, sustained, pulsed, controlled, targeted and programmed release formulations.

A compound of formula (I) may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed, sustained, pulsed, controlled, targeted, or programmed release formulations.

A compound of formula (I) may be combined with a soluble macromolecular entity, such as a cyclodextrin or a suitable derivative thereof or a polyethylene glycol-containing polymer, in order to improve its solubility, dissolution rate, taste-masking, bioavailability and/or stability in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO-A-91/11172, WO-A-94/02518 and WO-A-98/55148.

For administration to human patients, the total daily dose of a compound of formula (I) is typically in the range of from 1 mg to 1000 mg depending, of course, on the mode of administration and the potency of the selected compound. The total daily dose may be administered in single or divided doses and may, at the physician's discretion, fall outside of the typical range given herein.

These dosages are based on an average human subject having a weight of about 60 kg to 70 kg. The physician will readily be able to determine doses for subjects whose weight falls outside this range, such as infants and the elderly.

For the avoidance of doubt, references herein to "treatment" include references to curative, palliative and prophylactic treatment.

The biological activity of the alpha-2-delta ligands of the invention may be measured in a radioligand binding assay using [$^3$H]gabapentin and the $\alpha_2\delta$ subunit derived from porcine brain tissue based on the method given in *J. Biol. Chem.*, 1996, 271(10), 5768-5776). This assay is reproduced below.

[$^3$H]Gabapentin Binding Assay

Preparation of Brain Membranes

All solutions were maintained at 4° C. throughout. Pig brain cortex (up to 50 g) (fresh or frozen) was homogenised in 10 volumes of Buffer A (0.32 M Sucrose/1 mM EDTA/1 mM EGTA/10 mM Hepes/KOH, pH 7.4) by six strokes of a glass/teflon homogeniser at 600 r.p.m. After removal of the 1000 g×10 minute pellet, the supernatant was centrifuged at 40,000 g for 20 minutes and the resulting pellet was resuspended in 10 volumes of Buffer B (1 mM EDTA/1 mM EGTA/10 mM Hepes/KOH, pH 7.4). Following 30 minutes of continuous stirring, membranes were pelleted as above twice more by centrifugation with Buffer B, before a final re-suspension in approximately 3 volumes of storage buffer (1.25 mM EDTA/1.25 mM EGTA/25% Glycerol/12.5 mM Hepes/KOH, pH 7.4) to give a concentration of about 3 milligrams of protein per millilitre. Aliquots were stored at −80° C. until required.

Binding Assay Protocol:

Binding of [$^3$H]gabapentin to pig cerebral cortex membranes was carried out at 22° C. in 10 mM Hepes/KOH, pH 7.4 for 60 minutes. Non-specific binding (nsb) was defined as the binding obtained in the presence of 10 μM pregabalin. An assay volume of 250 μl was employed, comprising 200 μl of membranes, 25 μl test compound/buffer/nsb, 25 μl [$^3$H]gabapentin (final assay concentration ~10 nM). Separation of unbound radioligand was effected by rapid filtration under vacuum through cold 50 mM Tris/HCl, pH 7.4-dipped GF/B unifilter plates, using 2×1 ml of cold 50 mM Tris/HCl, pH 7.4. Plates were left to dry before addition of 50 μl/well microscint-40 and the amount of radioactivity bound determined using a TopCount scintillation counter. Results may be expressed as an $IC_{50}$ in terms of μM or nM.

All the Examples described below were tested in this alpha-2-delta assay and were found to have a binding affinity ($IC_{50}$) of 1 μM or less. For instance, (2S)-2-amino-4-ethyl-2-methylhexanoic acid (Example 1) had a binding affinity of 21 nM.

An alpha-2-delta receptor ligand may be usefully combined with another pharmacologically active compound, or with two or more other pharmacologically active compounds, particularly in the treatment of pain. For example, an alpha-2-delta receptor ligand, particularly a compound of formula (I), or a pharmaceutically acceptable salt or solvate thereof, as defined above, may be administered simultaneously, sequentially or separately in combination with one or more agents selected from:

- an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;
- a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin or zomepirac;
- a barbiturate sedative, e.g. amobarbital, aprobarbital, butabarbital, butabital, mephobarbital, metharbital, methohexital, pentobarbital, phenobartital, secobarbital, talbutal, theamylal or thiopental;
- a benzodiazepine having a sedative action, e.g. chlordiazepoxide, clorazepate, diazepam, flurazepam, lorazepam, oxazepam, temazepam or triazolam;
- an $H_1$ antagonist having a sedative action, e.g. diphenhydramine, pyrilamine, promethazine, chlorpheniramine or chlorcyclizine;
- a sedative such as glutethimide, meprobamate, methaqualone or dichloralphenazone;
- a skeletal muscle relaxant, e.g. baclofen, carisoprodol, chlorzoxazone, cyclobenzaprine, methocarbamol or orphrenadine;
- an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinone or cis-4-(phosphonomethyl)-2-piperidinecarboxylic acid;
- an alpha-adrenergic, e.g. doxazosin, tamsulosin, clonidine or 4-amino-6,7-dimethoxy-2-(5-methanesulfonamido-1,2,3,4-tetrahydroisoquinol-2-yl)-5-(2-pyridyl)quinazoline;
- a tricyclic antidepressant, e.g. desipramine, imipramine, amytriptiline or nortriptiline;
- an anticonvulsant, e.g. carbamazepine or valproate;
- a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]naphthridine-6-13-dione (TAK-637), 5-[[(2R,3S)-2-[(1R]-1-[3,5-bis(trifluoromethyl)phenyl]ethoxy-3-(4-fluorophenyl)-4-morpholinyl]methyl]-1,2-dihydro-3H-1,2,4-triazol-3-one (MK-869), lanepitant, dapitant or 3-[[2-methoxy-5-(trifluoromethoxy)phenyl]methylamino]-2-phenyl-piperidine (2S,3S);
- a muscarinic antagonist, e.g. oxybutin, tolterodine, propiverine, tropsium chloride or darifenacin;
- a selective COX-2 inhibitor, e.g. celecoxib, rofecoxib or valdecoxib;
- a non-selective COX inhibitor (preferably with GI protection), e.g. nitroflurbiprofen (HCT-1026);
- a coal-tar analgesic, in particular paracetamol;
- a neuroleptic such as droperidol;
- a vanilloid receptor agonist (e.g. resinferatoxin) or antagonist (e.g. capsazepine);
- a beta-adrenergic such as propranolol;
- a local anaesthetic such as mexiletine;
- a corticosteriod such as dexamethasone;
- a 5-HT receptor agonist or antagonist, particularly a $5\text{-HT}_{1B/1D}$ agonist such as eletriptan, sumatriptan, naratriptan, zolmitriptan or rizatriptan;
- a cholinergic (nicotinic) analgesic;
- Tramadol (trade mark);
- a PDEV inhibitor, such as sildenafil, vardenafil, taladafil, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine, or N-[1-(2-ethoxyethyl)-5-(N-ethyl-N-methylamino)-7-(4-methylpyridin-2-ylamino)-1H-pyrazolo[4,3-d]pyrimidine-3-carbonyl]methanesulfonamide;
- a canabinoid;
- metabotropic glutamate subtype 1 receptor (mGluR1) antagonist;
- a serotonin reuptake inhibitor such as sertraline;
- a noradrenaline reuptake inhibitor, especially a selective noradrenaline reuptake inhibitor such as (S,S)-reboxetine;
- an inducible nitric oxide synthase (iNOS) inhibitor such as S-[2-[(1-iminoethyl)amino]ethyl]-2-methyl-L-cysteine or (2S,5Z)-2-amino-2-methyl-7-[(1-iminoethyl)amino]-5-heptenoic acid;
- an acetylcholine esterase inhibitor such as donepezil;
- a dopamine type 2 (D2) antagonist such as ziprazidone;
- an prostaglandin $E_2$ subtype 4 (EP4) antagonist such as N-[({2-[4-(2-ethyl-4,6-dimethyl-1H-imidazo[4,5-c]pyridin-1-yl)phenyl]ethyl}amino)carbonyl]-4-methylbenzenesulfonamide or 4-[(1S)-1-({[5-chloro-2-(3-fluorophenoxy)pyridin-3-yl]carbonyl}amino)ethyl]benzoic acid;

and the pharmaceutically acceptable salts and solvates thereof.

Where a combination of active compounds is to be administered, two or more pharmaceutical compositions may conveniently be combined in the form of a kit suitable for co-administration of the compositions.

Such a kit comprises two or more separate pharmaceutical compositions, at least one of which contains an alpha-2-delta receptor antagonist, particularly a compound of formula (I), and means for separately retaining said compositions, such as a container, divided bottle, or divided foil packet. An example of such a kit is the familiar blister pack used for the packaging of tablets, capsules and the like.

Such a kit is particularly suitable for administering different dosage forms, for example, oral and parenteral formulations, for administering separate compositions at different dosage intervals, or for titrating separate compositions against one another. To assist compliance, the kit typically comprises directions for administration and may be provided with a so-called memory aid.

It will be appreciated that what the invention provides, and what will be claimed, is as follows:
(i) a compound of formula (II) or a pharmaceutically acceptable salt or solvate thereof;
(ii) a process for the preparation of a compound of formula (I) or a pharmaceutically acceptable salt or solvate thereof;
(iii) a pharmaceutical composition including a compound of formula (II) or a pharmaceutically acceptable salt or solvate thereof, together with a pharmaceutically acceptable excipient;
(iv) a compound of formula (II) or a pharmaceutically acceptable salt, solvate or composition thereof, for use as a medicament;
(v) the use of a compound of formula (I) or of a pharmaceutically acceptable salt, solvate or composition thereof, for the manufacture of a medicament to treat a disease for which an alpha-2-delta receptor ligand is indicated;
(vi) the use of a compound of formula (I) or of a pharmaceutically acceptable salt, solvate or composition thereof, for the manufacture of a medicament for the treatment of pain;
(vii) a method of treatment of a mammal, including a human being, with an alpha-2-delta receptor ligand, including treating said mammal with an effective amount of a compound of formula (I) or with a pharmaceutically acceptable salt, solvate or composition thereof;
(viii) a method of treatment of a mammal, including a human being, to treat pain, including treating said mammal with an effective amount of a compound of formula (I) or with a pharmaceutically acceptable salt, solvate or composition thereof;
(ix) certain novel intermediates disclosed herein; and
(x) a combination of a compound of formula (I) or (II) and one or more further pharmacologically active compounds.

The following Examples illustrate the preparation of compounds of formula (I).

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The mass spectra (MS) were recorded using either electrospray ionisation (ESI) or atmospheric pressure chemical ionisation (APCI). The following abbreviations have been used for common solvents: $CDCl_3$, deuterochloroform; $D_6$-DMSO, deuterodimethylsulphoxide; $CD_3OD$, deuteromethanol; THF, tetrahydrofuran. 'Ammonia' refers to a concentrated solution of ammonia in water possessing a specific gravity of 0.88. Where thin layer chromatography (TLC) has been used it refers to silica gel TLC using silica gel 60 $F_{254}$ plates, $R_f$ is the distance travelled by a compound divided by the distance travelled by the solvent front on a TLC plate. Microwave radiation was performed using machines with a power range of 15 to 300 W at 2.45 GHz, the actual power supplied varying during the course of the reaction to maintain a constant temperature. LCMS indicates liquid chromatography mass spectrometry ($R_t$=retention time).

EXAMPLE 1

(2S)-2-Amino-4-ethyl-2-methylhexanoic acid

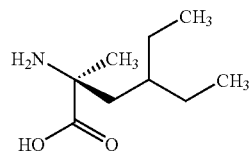

Method A

Peariman's catalyst (0.15 g) was added to a solution of (3S,5S)-3-(2-ethylbutyl)-3-methyl-5-phenylmorpholin-2-one (0.15 g, 0.54 mmol, Preparation 1) in ethanol (5 ml) and 1 molar aqueous hydrochloric acid (1 ml). The reaction was stirred under hydrogen gas (414 kPa, 60 psi) at room temperature for 24 hours. The reaction mixture was filtered through arbocel and washed with ethanol (20 ml). The liquor was evaporated under reduced pressure and the residue was partitioned between dichloromethane (50 ml) and water (20 ml). The organic layer was removed and the aqueous phase was extracted with more dichloromethane (50 ml). The aqueous phase was evaporated under reduced pressure to give a yellow solid. The material was purified by ion exchange chromatography on Dowex 50 WX8 resin, eluting with 0.88 aqueous ammonia:water (2:98 to 14:86) to give the title compound as a white crystalline solid (30 mg).

$^1$HNMR ($CD_3OD$, 400 MHz) δ: 0.83-0.89 (m, 6H), 1.29-1.43 (m, 8H), 1.58-1.62 (dd, 1H), 1.81-1.86 (dd, 1H).

LRMS (ESI): m/z 174 [M+H$^+$], 172 [M−H$^-$].

Method B 20 wt % Palladium hydroxide on carbon (1.0 g; 50 wt % water wet) was added to a suspension of 4-ethyl-2-(2-hydroxy-1-phenyl-ethylamino)-2-methyl-hexanoic acid (Preparation 10, 10.0 g; 34.0 mmol) in propan-2-ol and water (4:1; 200 ml). The vessel was purged three times with nitrogen then hydrogen before the suspension was then stirred under a hydrogen gas atmosphere (60 psi) at 80° C. for 4 hours. The resultant solution was then filtered through Arbocel® and washed with propan-2-ol and water (4:1; 20 ml). Propan-2-ol and water (4:1; 100 ml) was added and then distilled under reduced pressure collecting 260 ml of solvent. A further portion of propan-2-ol (100 ml) was added and a further 100 ml of solvent was removed by distillation under reduced pressure. A third portion of propan-2-ol (100 ml) was added and a further 40 ml of solvent removed by distillation under reduced pressure. A viscous white slurry was then observed which was cooled to 22° C. The resultant slurry was stirred at 22° C. for 30 minutes and the solid then isolated by filtration. The filter cake was washed with propan-2-ol (20 ml) and dried at 45° C. under vacuum overnight to give the title compound (3.5 g crude weight, 98% purity, 20.2 mmol, 60% yield); $^1$H-NMR (CD$_3$OD, 300 MHz), δ: 0.86 (6H, q), 1.28-1.40 (5H, m), 1.44 (3H, s), 1.57-1.63 (1H, dd), 1.80-1.87 (1H, dd).

Example 1.1

(2S)-2-Amino-4-ethyl-2-methylhexanoic acid benzene sulphonic acid salt

A solution of benzene sulphonic acid (9.5 g) in acetonitrile (50 ml) was added to a suspension of (2S)-2-Amino-4-ethyl-2-methylhexanoic acid (10 g, 0.057 mol, Example 1) in acetonitrile (175 ml) and the mixture heated until dissolved. The solution was filtered whilst hot and allowed to cool overnight to give the title compound as fine white needles, (16.5 g, 86%)
$^1$HNMR (CD3OD, 400 MHz) δ: 0.87 (m, 6H), 1.36 (m, 4H), 1.41 (m, 1H), 1.54 (m, 3H), 1.75 (m, 1H), 1.88 (m, 1H), 7.42 (m, 3H), 7.83 (m, 2H), 4 exchangeable not seen.

Example 1.2

(2S)-2-Amino-4-ethyl-2-methylhexanoic acid p-toluenesulphonate salt

A solution of p-toluene sulphonic acid (54 mg, 0.28 mmol) in acetonitrile (1 ml) was added to a suspension of (2S)-2-Amino-4-ethyl-2-methylhexanoic acid (50 mg, 0.28 mmol, Example 1) in acetonitrile (1 ml) and the mixture heated until dissolved. The solution was filtered whilst hot and allowed to cool overnight to give the title compound as fine white needles, (69 mg, 70%)
$^1$HNMR (CD3OD, 400 MHz) δ: 0.88 (m, 6H), 1.36 (m, 5H), 1.54 (s, 3H), 1.75 (m, 1H), 1.90 (m, 1H), 2.36 (s, 3H), 7.22 (d, 2H), 7.70 (d, 2H), 4 exchangeable not seen.

Example 1.3

(2S)-2-Amino-4-ethyl-2-methylhexanoic acid hydrochloride salt

A solution of HCl in methanol was prepared by cautiously adding acetyl chloride (0.04 ml,) to methanol (1 ml). The cooled solution was added to a suspension of (2S)-2-Amino-4-ethyl-2-methylhexanoic acid (100 mg, 0.56 mmol, Example 1) in methanol (1 ml) and the mixture warmed until dissolved, then evaporated under reduced pressure. The resulting hydrochloride salt was recrystallised from methanol/acetonitrile to give a white solid (63 mg, 52%)
$^1$HNMR (CD3OD, 400 MHz) δ: 0.87 (m, 6H), 1.36 (m, 4H), 1.43 (m, 1H), 1.55 (s, 3H), 1.75 (m, 1H), 1.90 (m, 1H), 4 exchangeable not seen

EXAMPLE 2

2,5,5-Trimethyl-L-norleucine

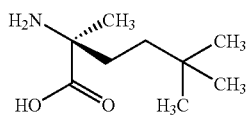

The title compound was prepared according to the procedure outlined in Example 1 from (3S,5S)-3-(3,3-dimethylbutyl)-3-methyl-5-phenylmorpholin-2-one (0.394 g, 1.43 mmol, Preparation 2). The product (0.138 g) was obtained as a white crystalline solid.
$^1$HNMR (CD$_3$OD, 400 MHz) δ: 0.91 (s, 9H), 1.17-1.25 (m, 1H), 1.28-1.36 (m, 1H), 1.44 (s, 3H), 1.59-1.67 (m, 1H), 1.83-1.91 (m, 1H).
LRMS (ESI): m/z 174 [M+H$^+$], 172 [M-H$^-$].

EXAMPLE 3

(2S)-2-Amino-3-cyclopentyl-2-methylpropanoic acid

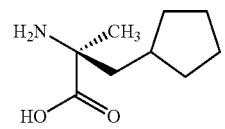

The title compound was prepared according to the procedure outlined in Example 1 from (3S,5S)-3-(cyclopentylmethyl)-3-methyl-5-phenylmorpholin-2-one (0.426 g, 1.56 mmol, Preparation 3). The product (0.157 g) was obtained as a white crystalline solid.
$^1$HNMR (CD$_3$OD, 400 MHz) δ: 1.08-1.22 (m, 2H), 1.44 (s, 3H), 1.48-1.68 (m, 4H), 1.74-2.00 (m, 5H).
LRMS (ESI): m/z 174 [M+H$^+$], 172 [M-H$^-$].

EXAMPLE 4

(2S)-2-Amino-5-ethyl-2-methylheptanoic acid

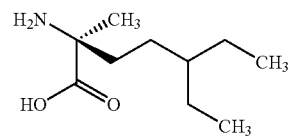

The title compound was prepared according to the procedure outlined in Example 1 from (3S,5S)-3-(3-ethylpentyl)-3-methyl-5-phenylmorpholin-2-one (Preparation 4). The product was obtained as a white crystalline solid.
$^1$HNMR (CD$_3$OD, 400 MHz) δ: 0.85-0.92 (m, 6H), 1.16-1.48 (m, 7H), 1.56 (s, 3H), 1.72-1.99 (m, 2H).
LRMS (ESI): m/z 188 [M+H$^+$], 186 [M-H$^-$].

EXAMPLE 5

(2S)-2-Amino-3-cyclobutyl-2-methylpropanoic acid

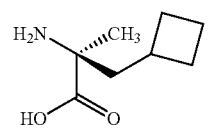

Pearlman's catalyst (0.5 g) was added to a solution of (3S,5S)-3-(cyclobutylmethyl)-3-methyl-5-phenylmorpholin-2-one (0.445 g, 1.7 mmol, Preparation 5) in ethanol (15 ml), water (2 ml) and trifluoroacetic acid (0.5 ml). The reaction was stirred under hydrogen gas (414 kPa, 60 psi) at room temperature for 24 hours. The reaction mixture was filtered through Arbocel® and washed with ethanol (20 ml). The liquor was evaporated under reduced pressure and the residue was partitioned between dichloromethane (50 ml) and water (50 ml). The organic layer was removed and the aqueous phase was extracted with more dichloromethane (50 ml). The water layer was evaporated under reduced pressure to give a yellow solid. The product was purified by ion exchange chromatography on Dowex 50 WX8 resin, eluting with 0.88 aqueous ammonia:water (2:98 to 14:86) to give the title compound (0.034 g) as a white solid.

$^1$HNMR (CD$_3$OD, 400 MHz) δ: 1.40 (s, 3H), 1.69-1.84 (m, 6H), 2.04-2.17 (m, 2H), 2.41-2.54 (m, 1H).

LRMS (ESI): m/z 158 [M+H$^+$], 156 [M–H$^-$].

EXAMPLE 6

(2S,5R)-2-Amino-2,5-dimethylheptanoic acid

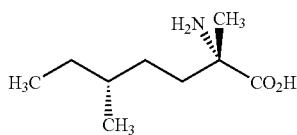

A solution of the compound of Preparation 8 (1.10 g) in dioxane (3 ml) and 6N aqueous hydrochloric acid (15 ml) was heated under reflux for 16 hours. The solution was then allowed to cool to room temperature, the solvent was evaporated and the residue was redissolved in 2 ml of water. A column of DOWEX-50X8-200 (25 g) was washed with 250 ml of deionised water. The crude product was then loaded and the column was eluted with 250 ml of deionised water and then 250 ml of 10% aqueous ammonia. The basic fractions were evaporated to give the title compound (0.18 g) as a white solid.

$^1$HNMR (CD$_3$OD, 400 MHz) δ: 0.89 (6H, m), 1.08-1.24 (2H, m), 1.26-1.49 (6H, m), 1.56-1.65 (1H, m), 1.87-1.96 (1H, m).

LRMS (APCI): m/z 174 [M+H$^+$].

EXAMPLE 7

(4S)-2,4-Dimethyl-L-norleucine

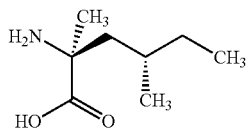

The title compound was prepared according to the procedure outlined in Example 1 from (3S,5S)-3-methyl-3-[(2S)-2-methylbutyl]-5-phenylmorpholin-2-one (0.586 g, 2.24 mmol, Preparation 9). The product (0.018 g) was obtained as a white crystalline solid.

$^1$HNMR (CD$_3$OD, 400 MHz) δ: 0.90-0.92 (m, 3H), 0.94-0.95 (m, 3H), 1.17-1.40 (m, 2H), 1.45 (s, 3H), 1.50-1.58 (bs, 1H), 1.69-1.81 (m, 1H), 1.70-1.83 (m, 1H).

LRMS (ESI): m/z 262 [M+H$^+$].

The following preparations show how intermediates used in the preparation of the Examples described above may themselves be synthesised.

Preparation 1

(3S,5S)-3-(2-Ethylbutyl)-3-methyl-5-phenylmorpholin-2-one

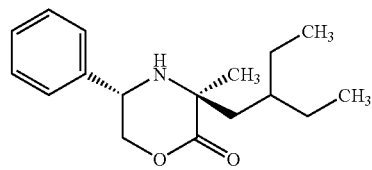

Boron trifluoride etherate (5.85 ml, 46 mmol) was added slowly to a solution of (5S)-3-methyl-5-phenyl-5,6-dihydro-2H-1,4-oxazin-2-one (4.35 g, 23 mmol, see WO-A-02/051983) in tetrahydrofuran at −78° C. The solution was stirred for 50 minutes and then a solution of the Grignard reagent prepared from 3-(bromomethyl)pentane (10.9 g, 66 mmol) and magnesium turnings (2.5 g, 99 mmol) in ether (250 ml) was added over 40 minutes. The reaction mixture was stirred for a further 75 minutes at −78° C. then allowed to warm to −20° C. and quenched with saturated aqueous ammonium chloride (100 ml). More tetrahydrofuran (100 ml) was added and the organic layer was separated from the aqueous layer. The organic layer was dried (MgSO$_4$) and concentrated under reduced pressure. The residue was purified by column chromatography on silica gel using an elution gradient of pentane to pentane:ether (30:70) to afford the title compound as a white solid (3.21 g).

$^1$HNMR (CDCl$_3$, 400 MHz) δ: 0.79 (q, 6H), 1.26-1.35 (m, 5H), 1.41 (s, 3H), 1.63 (dd, 1H), 1.91 (dd, 1H), 4.17-4.26 (m, 1H), 4.28-4.35 (m, 2H), 7.25-7.36 (m, 5H).

LRMS (ESI): m/z 276 [M+H$^+$].

Preparation 2

(3S,5S)-3-(3,3-Dimethylbutyl)-3-methyl-5-phenylmorpholin-2-one

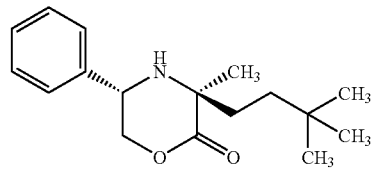

A suspension of Rieke Magnesium (343 mg, 14.1 mmol) in tetrahydrofuran (13.7 ml) was added to a solution of 1-iodo-3,3-dimethylbutane in diethylether (50 ml) over a period of twenty minutes and the reaction was stirred for 40 minutes at room temperature. The Grignard reagent solution and (5S)-3-methyl-5-phenyl-5,6-dihydro-2H-1,4-oxazin-2-one (1 g, 5.28 mmol, see WO-A-02/051983) were used according to the method of Preparation 1 to generate the title compound. The total amount of compound synthesised was 0.394 g.

$^1$HNMR (CDCl$_3$, 400 MHz) δ: 0.91 (s, 9H), 1.13-1.31 (m, 3H), 1.42 (s, 3H), 1.67-1.77 (bs, 1H), 2.02-2.10 (m, 1H), 4.31-4.43 (m, 3H), 7.34-7.46 (m, 5H).

LRMS (ESI): m/z 276 [M+H$^+$].

Preparation 3

(3S,5S)-3-(Cyclopentylmethyl)-3-methyl-5-phenyl-morpholin-2-one

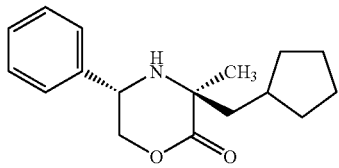

The compound was prepared according to the procedure outlined in Preparation 1 using (5S)-3-methyl-5-phenyl-5,6-dihydro-2H-1,4-oxazin-2-one (1 g, 5.28 mmol, see WO-A-02/051983) and (iodomethyl)cyclopentane. The total amount of compound synthesised was 0.426 g.

¹HNMR (CDCl₃, 400 MHz) δ: 1.12-1.22 (m, 2H), 1.43-1.65 (m, 8H), 1.78-1.94 (m, 4H), 2.13-2.18 (m, 1H), 4.23-4.42 (m, 3H), 7.31-7.45 (m, 5H).

LRMS (ESI): m/z 274 [M+H⁺].

Preparation 4

(3S,5S)-3-(3-Ethylpentyl)-3-methyl-5-phenylmorpholin-2-one

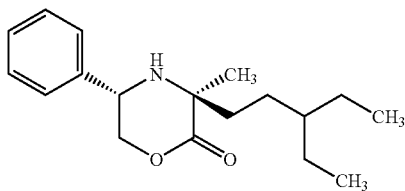

The title compound was prepared from (5S)-3-methyl-5-phenyl-5,6-dihydro-2H-1,4-oxazin-2-one (0.454 g, 2.39 mmol, see WO-A-02/051983) and 1-bromo-3-ethylpentane (see *Bull. Soc. Chim. Fr.*, 1975, 201-205) according to the procedure outlined in Preparation 1. The total amount of compound synthesised was 0.07 g.

¹HNMR (CDCl₃, 400 MHz) δ: 0.91 (s, 9H), 1.13-1.31 (m, 3H), 1.42 (s, 3H), 1.67-1.77 (bs, 1H), 2.02-2.10 (m, 1H), 4.31-4.43 (m, 3H), 7.34-7.46 (m, 5H).

LRMS (ESI): m/z 276 [M+H⁺].

Preparation 5

(3S,5S)-3-(Cyclobutylmethyl)-3-methyl-5-phenyl-morpholin-2-one

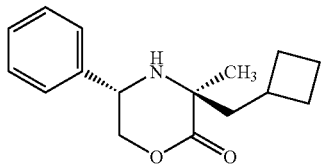

The title compound was prepared from (5S)-3-methyl-5-phenyl-5,6-dihydro-2H-1,4-oxazin-2-one (1 g, 5.28 mmol, see WO-A-02/051983) and (bromomethyl)cyclobutane according to the procedure outlined in Preparation 1. The total amount of compound synthesised was 0.445 g.

¹HNMR (CDCl₃, 400 MHz) δ: 1.43 (s, 3H), 1.73-1.82 (m, 2H), 1.86-1.92 (m, 2H), 2.02-2.12 (m, 2H), 2.14-2.19 (m, 1H), 2.43-2.52 (m, 1H), 4.22-4.27 (m, 1H), 4.33-4.37 (m, 2H), 7.31-7.43 (m, 5H).

LRMS (ESI): m/z 260 [M+H⁺].

Preparation 6

(5R)-5-Methylheptan-2-one

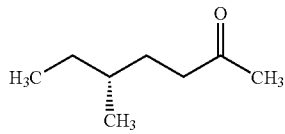

Dicyclohexyl carbodiimide (9.51 g, 46.1 mmol), N,N'-dimethyl-4-aminopyridine (1.13 g, 9.2 mmol) and triethylamine (6.4 ml, 46.1 mmol) were added to a solution of Meldrum's acid (6.64 g, 46.1 mmol) in dichloromethane (150 ml). (4R)-4-Methylhexanoic acid (6 g, 46.1 mmol) was added and the reaction mixture was stirred overnight. The reaction mixture was filtered and the solid was washed with dichloromethane (2×100 ml). The filtrate and washings were combined and evaporated under reduced pressure to give an orange oil. Acetic acid (50 ml) and water (50 ml) were added and the reaction was heated under reflux overnight. After the solution had cooled to room temperature it was extracted with pentane (100 ml). The organic extract was dried (MgSO₄) and evaporated to give a residue that was purified by column chromatography on silica gel using an elution gradient of pentane to pentane:diethyl ether 19:1 to give the title compound (2.8 g) as a pale yellow oil.

¹HNMR (CDCl₃, 400 MHz) δ: 0.82-0.88 (6H, m), 1.07-1.19 (1H, m), 1.25-1.41 (3H, m), 1.54-1.64 (1H, m), 2.12 (3H, s), 2.34-2.47 (2H, m).

Preparation 7

N-[(1E,4R)-1,4-dimethylhexylidene]-(S)-2-methyl-propane-2-sulfinamide

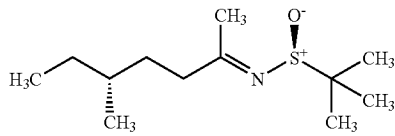

A solution of (5R)-5-methylheptan-2-one (3 g, 23.4 mmol) in tetrahydrofuran (10 ml) was added to a solution of (S)-2-methylpropane-2-sulfinamide and titanium tetraethoxide (9.8 ml, 46.8 mmol) in tetrahydrofuran. The solution was stirred at 50° C. for 20 hours. The reaction mixture was allowed to cool to room temperature, diluted with ethyl acetate (50 ml) and then poured into brine (100 ml).

The layers were stirred vigorously for 2 minutes and then filtered. The organic layer was separated from the aqueous layer and dried (MgSO₄). The solvent was evaporated under reduced pressure and the residue was purified by column chromatography on silica gel using an elution gradient of 1:9 ethyl acetate:pentane then 3:17 ethyl acetate:pentane. This gave the title compound as a pale yellow oil (3.6 g).

¹HNMR (CDCl₃, 400 MHz) δ: 0.82-0.91 (6H, m), 1.10-1.23 (10H, m), 1.29-1.43 (3H, m), 1.54-1.65 (1H, m), 2.15 (0.6H, s), 2.30 (2.4H, s), 2.32-2.72 (2H, m).

LRMS: m/z ESI 232 [M+H⁺].

Preparation 8

N-[(1S,4R)-1-cyano-1,4-dimethylhexyl]-2-methyl-propane-(S)-2-sulfinamide

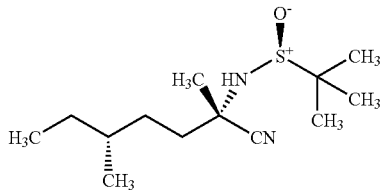

Isopropanol (0.63 ml, 8.2 mmol) was added to a mixture of a 1 molar solution of diethylaluminium cyanide in toluene (12.3 ml) and tetrahydrofuran (5 ml). The mixture was stirred at room temperature for 10 min and then cooled to −78° C. A solution of the compound of Preparation 7 (1.9 g, 8.2 mmol) in tetrahydrofuran (20 ml) was added dropwise over 2 minutes. The reaction was then stirred at −78° C. for 5 minutes and at room temperature for 90 minutes. The reaction mixture was then cooled to −20° C. and poured onto a vigorously stirred mixture of ethyl acetate (100 ml) and water (100 ml). The mixture was filtered through Arbocel® and the ethyl acetate layer was separated and dried (MgSO$_4$). The solvent was evaporated under reduced pressure and the residue was purified by column chromatography on silica gel using an elution gradient of 1:4 ethyl acetate:pentane then 3:7 ethyl acetate:pentane. This gave the title compound as a white solid (1.10 g).

$^1$HNMR (CDCl$_3$, 400 MHz) δ: 0.86-0.93 (6H, m), 1.13-1.26 (10H, m), 1.29-1.44 (3H, m), 1.48-1.57 (2H, m), 1.64 (3H, s), 1.81-1.98 (2H, m), 3.41 (1H, s).

LRMS (APCI): m/z 259 [M+H]$^+$.

Preparation 9

(3S,5S)-3-Methyl-3-[(2S)-2-methylbutyl]-5-phenyl-morpholin-2-one

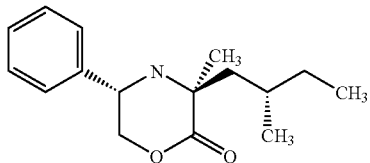

The title compound was prepared from (5S)-3-methyl-5-phenyl-5,6-dihydro-2H-1,4-oxazin-2-one (1 g, 5.28 mmol, see WO-A-02/051983) and (2S)-1-iodo-2-methylbutane according to the procedure outlined in Preparation 1. The total amount of compound synthesised was 0.586 g.

$^1$HNMR (CDCl$_3$, 400 MHz) δ: 0.85-0.88 (m, 3H), 0.94-0.96 (m, 3H), 1.17-1.40 (m, 3H), 1.46 (s, 3H), 1.60 (bs, 1H), 1.73-1.78 (m, 1H), 1.88-1.93 (m, 1H), 4.22-4.42 (m, 3H), 7.28-7.42 (m, 5H).

LRMS (ESI): m/z [M+H]$^+$.

Preparation 10

4-Ethyl-2-(2-hydroxy-1-phenyl-ethylamino)-2-methyl-hexanoic acid

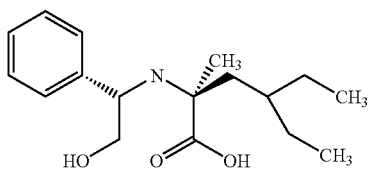

To a solution of (5S)-3-methyl-5-phenyl-5,6-dihydro-2H-[1,4]oxazin-2-one (5 g, 26.4 mmol, see WO-A-02/051983) in anhydrous 2-methyltetrahydrofuran (50 ml) was added boron trifluoride tetrahydrofuran complex (5.8 ml, 52.8 mmol) with stirring under nitrogen at −78° C. The resultant solution was then stirred at −78° C. for 1 hour. (2-Ethylbutyl)magnesium bromide as a solution in tetrahydrofuran (170 ml, 0.16 M, 27.7 mmol) was then added maintaining the temperature below −60° C. during the addition. The resultant solution was stirred at −78° C. for a further 2 hours. Acetic acid (0.6 ml 10.6 mmol) was then added and the solution warmed to 22° C. Saturated aqueous ammonium chloride (50 ml) was then added followed by water (100 ml). The phases were separated and the organic phase retained. The resultant solution was then distilled to dryness under vacuum. Toluene (75 ml) was then added and the organic solution was washed with water (25 ml) then saturated aqueous sodium chloride solution (25 ml) and the phases separated and the organic phase retained. Aqueous hydrochloric acid (100 ml, 1.5 M) was then added and the resultant biphasic mixture warmed to 30° C. and stirred for 2 hours. The phases were separated and the aqueous phase retained. Aqueous sodium hydroxide (47% w/w, 6 ml then 2M, 16 ml) was then added to give a pH of 5 by pH paper. The resultant slurry was stirred at 22° C. for 30 minutes and the solid was then isolated by filtration. The filter cake was washed with water (25 ml) and dried at 60° C. overnight under vacuum to give the title compound (4.1 g crude weight, 95% purity, 14.0 mmol, 53% yield): mp 149° C.; $^1$H-NMR (CD$_3$OD, 300 MHz), δ: 0.83 (3H, t), 0.90 (3H, t), 1.06 (3H, s), 1.31-1.54 (5H, m) 1.73 (2H, d), 4.40 (1H, t), 7.46-7.50 (5H, m); LRMS (ES): m/z 293 [M]$^+$.

The invention claimed is:

1. (2S)-2-Amino-4-ethyl-2-methylhexanoic acid or a pharmaceutically acceptable salt thereof.

2. A compound of claim 1 wherein the compound is (2S)-2-amino-4-ethyl-2-methylhexanoic acid.

3. A compound of claim 1 wherein the compound is a pharmaceutically acceptable salt of (2S)-2-amino-4-ethyl-2-methylhexanoic acid.

4. A compound of claim 3 wherein the compound is a benzene sulphonic salt of (2S)-2-amino-4-ethyl-2-methylhexanoic acid.

5. A compound of claim 3 wherein the compound is a p-toluenesulphonate salt of (2S)-2-amino-4-ethyl-2-methylhexanoic acid.

6. A compound of claim 3 wherein the compound is a hydrochloride salt of (2S)-2-amino-4-ethyl-2-methylhexanoic acid.

7. A pharmaceutical composition comprising (2S)-2-amino-4-ethyl-2-methylhexanoic acid, or a pharmaceutically acceptable salt thereof, and a pharmaceutically acceptable excipient.

8. A pharmaceutical composition of claim 7 wherein the composition comprises (2S)-2-amino-4-ethyl-2-methylhexanoic acid.

9. A pharmaceutical composition of claim 7 wherein the composition comprises a pharmaceutically acceptable salt of (2S)-2-amino-4-ethyl-2-methylhexanoic acid.

* * * * *